(12) United States Patent
Mettuvalavu Palanisamy et al.

(10) Patent No.: US 12,741,131 B2
(45) Date of Patent: Sep. 22, 2026

(54) LEAK-PROOF FLUID CONNECTION SYSTEM

(71) Applicant: CareFusion 303, Inc., San Diego, CA (US)

(72) Inventors: Karthikeyan Mettuvalavu Palanisamy, Gobichettipalayam (IN); Jayavignesh Mathimaran, Chennai (IN); Sudhakara Bathula, Andhra Pradesh (IN); Yetirajendra Daroji, Chennai (IN)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 19/002,497

(22) Filed: Dec. 26, 2024

(65) Prior Publication Data

US 2026/0183525 A1 Jul. 2, 2026

(51) Int. Cl.

*A61M 39/02* (2006.01)
*F16K 7/06* (2006.01)
*F16L 33/18* (2006.01)

(52) U.S. Cl.

CPC ........... *A61M 39/0208* (2013.01); *F16K 7/06* (2013.01); *F16L 33/18* (2013.01); *A61M 39/02* (2013.01); *A61M 2207/10* (2013.01); *Y10T 137/7889* (2015.04)

(58) Field of Classification Search

CPC ...... F16K 7/04; F16K 7/06; Y10T 137/87627; Y10T 137/87676
USPC ....................................... 16/2.1; 604/247, 83
See application file for complete search history.

(56) References Cited

U.S. PATENT DOCUMENTS 3,416,567 A * 12/1968 Tauberman ........... F16K 11/027 137/853
4,819,684 A * 4/1989 Zaugg .................. A61M 39/02 137/853
5,098,405 A * 3/1992 Peterson ............... A61M 39/02 604/246

(Continued)

FOREIGN PATENT DOCUMENTS

EP 0370997 A2 5/1990
JP S62243563 A 10/1987

OTHER PUBLICATIONS

International Search Report and Written Opinion for Application No. PCT/US2025/050835, dated Feb. 16, 2026, 13 pages.

*Primary Examiner* — Robert K Arundale
(74) *Attorney, Agent, or Firm* — MASCHOFF BRENNAN

(57) ABSTRACT

A needleless fluid delivery device can be coupled to a valve to deliver fluid to a patient. When the device is withdrawn from the valve, the fluid inside the valve can leak out of the valve. This problem can be addressed with an anti-leak valve. The anti-leak valve can include a housing having a reception lumen and a delivery lumen that is transverse to the reception lumen. A guide bush is positioned in the reception lumen, and a silicon tube bears outwardly against the delivery lumen. When the device is inserted into the reception lumen, the device displaces the guide bush and compresses the silicon tube. This compression fluidly connects a hole in the guide bush to the delivery lumen, which facilitates delivery of the fluid. When the device is removed, the silicon tube seals the delivery lumen and restricts fluid from leaking out of the valve.

15 Claims, 5 Drawing Sheets

(56) References Cited

U.S. PATENT DOCUMENTS

| | | | | | |
|---|---|---|---|---|---|
| 5,407,437 | A * | 4/1995 | Heimreid | A61M 39/02 | 604/83 |
| 5,512,043 | A * | 4/1996 | Verkaart | A61M 39/02 | 137/853 |
| 5,810,768 | A * | 9/1998 | Lopez | A61M 39/02 | 604/83 |
| 6,083,194 | A | 7/2000 | Lopez | | |
| 8,622,972 | B2 * | 1/2014 | Nystrom | A61M 39/0606 | 604/167.03 |
| 11,992,647 | B2 * | 5/2024 | Natesan | A61M 25/0606 | |
| 2006/0213563 | A1 * | 9/2006 | Peppel | A61M 39/02 | 137/605 |
| 2007/0089787 | A1 * | 4/2007 | Patzer | A61M 39/223 | 137/111 |
| 2009/0124983 | A1 * | 5/2009 | Ferrari | A61M 39/02 | 604/247 |
| 2013/0090607 | A1 * | 4/2013 | McKinnon | A61M 39/0693 | 604/247 |
| 2016/0008569 | A1 * | 1/2016 | Harding | A61M 25/007 | 604/256 |
| 2025/0032757 | A1 * | 1/2025 | Boud | A61M 25/0097 | |

* cited by examiner 10
100
102
12
202
200
204
300
16
108

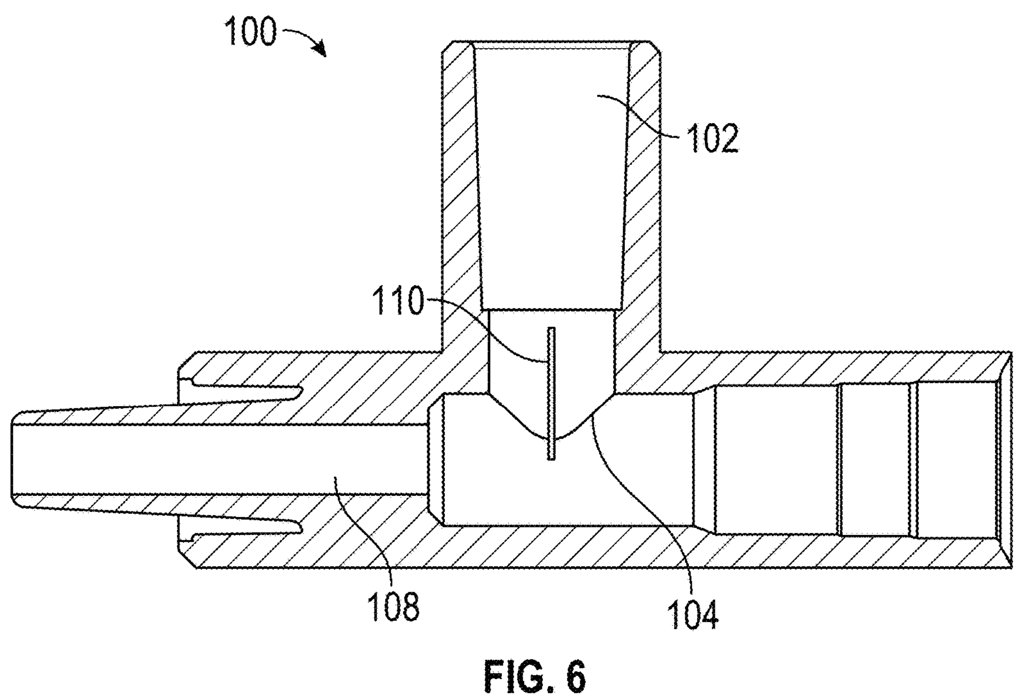
FIG. 6
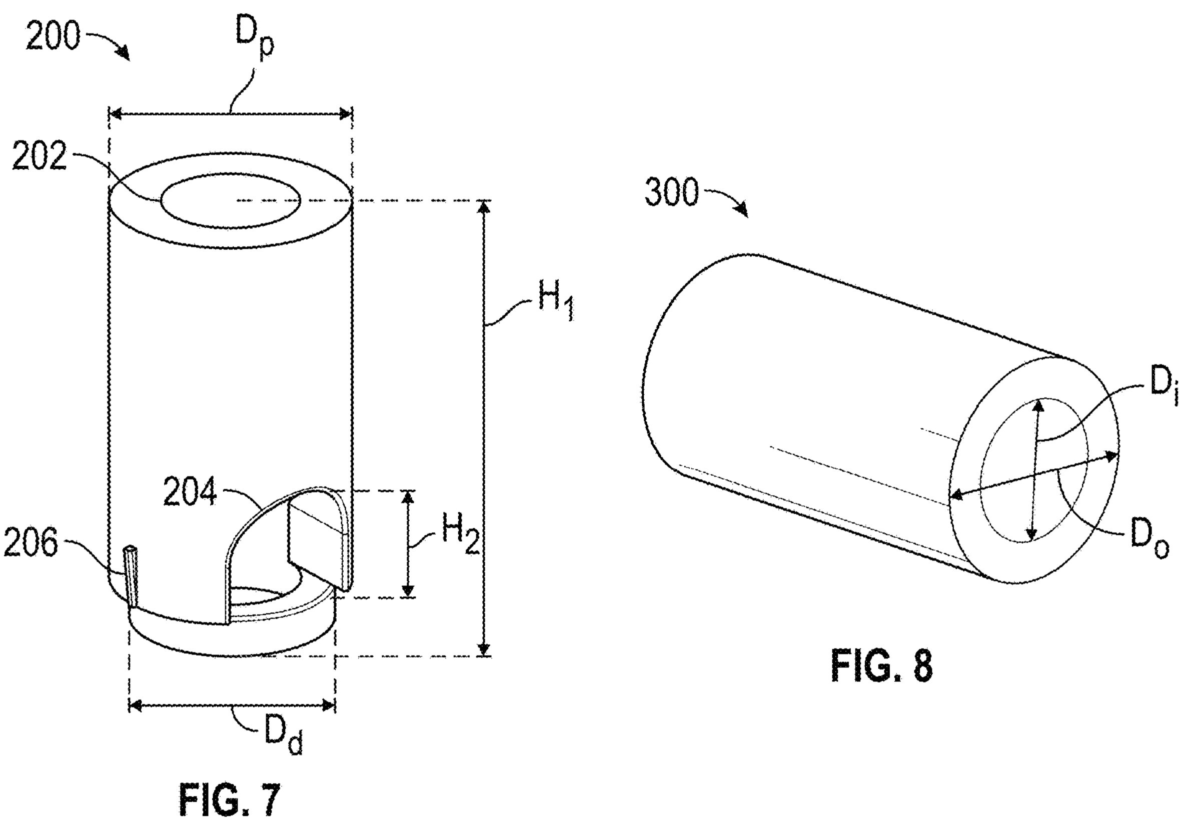
FIG. 7
FIG. 8

LEAK-PROOF FLUID CONNECTION SYSTEM

TECHNICAL FIELD

The present disclosure relates generally to medical fluid valves and, more particularly, to valves modified to control medical fluid and connect to needleless fluid connector systems.

BACKGROUND

A fluid connection system can include a stopcock with various ports configured to couple with needleless fluid connectors, such as neutral displacement needle-free connectors. The ports can connect directly to fluid delivery devices or can connect indirectly to fluid delivery devices via extension tubing. For example, one port of a stopcock can connect directly to a syringe, while another port can connect to an extension tube that is fluidly connected to additional ports and other fluid delivery devices.

SUMMARY

A fluid connection system can be used to connect multiple fluid delivery devices and ports, such as stopcocks, intravenous (IV) cannulas, IV delivery sets, extension tubes, valves, syringes, etc. In particular, a syringe (or other fluid delivery device) can be inserted into a valve housing to deliver fluid to the fluid connection system. When the syringe is withdrawn (either intentionally or by accident) from the valve housing, fluid (e.g., medication) can leak out of the valve housing because withdrawal of the syringe exposes the fluid to the surrounding environment. Therefore, a valve housing that prevents fluid from leaking upon removal of the syringe is desirable.

Some embodiments of the present disclosure are directed to an anti-leak injection port for a fluid connection device, the injection port comprising a housing comprising a reception lumen and a delivery lumen, wherein the delivery lumen is transverse to the reception lumen and intersects a distalmost end of the reception lumen; a guide bush disposed within the reception lumen and configured to receive a fluid delivery device, wherein the guide bush comprises an inner lumen and an aperture fluidly connected to the inner lumen; and a resilient member disposed within the delivery lumen and configured to restrict fluid flow through the delivery lumen in a default position and to fluidly connect the fluid delivery device and the delivery lumen in a flow position, wherein the resilient member is configured to be compressed into the flow position when the guide bush receives the fluid delivery device.

In some embodiments, the injection port is configured to fluidly connect the fluid delivery device to one or more of an extension tube, an IV cannula, or a stopcock.

In some embodiments, the housing comprises slots, and the guide bush comprises keys that are movably coupled to the slots. Optionally, the slots are positioned at a distal portion of the reception lumen and adjacent to the delivery lumen. Optionally, the slots and the keys are configured to facilitate continuous contact between the guide bush and the resilient member. Optionally, the keys are configured to advance distally along the slots when the guide bush receives the fluid delivery device and are configured to slide proximally along the slots when the fluid delivery device is withdrawn from the guide bush.

In some embodiments, the guide bush comprises a material that is more rigid than the resilient member.

In some embodiments, the guide bush receives the fluid delivery device at a proximal end of the guide bush and contacts the resilient member at a distal end of the guide bush.

In some embodiments, the guide bush is configured to be advanced distally by the fluid delivery device to compress the resilient member from the default position into the flow position.

In some embodiments, the guide bush has a first height, the aperture has a second height, and the ratio of the first height to the second height is about 3.

In some embodiments, the aperture is positioned at a distal portion of the guide bush.

In some embodiments, the aperture is configured to fluidly connect the inner lumen and the delivery lumen when the guide bush receives the fluid delivery device and compresses the resilient member into the flow position.

In some embodiments, the resilient member comprises a hollow cylinder.

In some embodiments, the hollow cylinder comprises an inner diameter and an outer diameter, and the ratio of the outer diameter to the inner diameter is about 1.5.

In some embodiments, the resilient member is configured to bear radially outward against the delivery lumen.

In some embodiments, the resilient member comprises an elastic material and is configured to resiliently transition from the flow position to the default position when the fluid delivery device is withdrawn from the guide bush.

Other embodiments of the present disclosure are directed to a guide bush for an anti-leak injection port. The guide bush is configured to be movably coupled to a housing and comprising an inner lumen, an aperture that is fluidly connected to the inner lumen, and keys protruding from an outer surface of the guide bush, wherein the guide bush is configured to receive a fluid delivery device be distally advanced to displace a resilient member coupled to the housing and facilitate fluid flow through the housing.

In some embodiments, the keys are configured to movably couple with slots in the housing of the anti-leak injection port.

In some embodiments, the aperture is positioned on a distal portion of the guide bush.

The present disclosure also discloses a method for manufacturing an anti-leak injection port. The method comprises first providing a housing comprising a reception lumen, slots on a surface of a distal portion of the reception lumen, and a delivery lumen that is transverse to the reception lumen and intersects a distalmost end of the reception lumen. Next, the method comprises providing a resilient member, wherein the resilient member is hollow and cylindrical, and positioning the resilient member within the delivery lumen, wherein the resilient member bears outwardly against the delivery lumen in a default position. Next, the method involves providing a guide bush comprising an inner lumen, an aperture fluidly connected to the inner lumen, and keys protruding from an outer surface of a distal portion of the guide bush. After providing the guide bush, the method comprises positioning a guide bush within the reception lumen such that the keys are movably coupled to the slots and a distal end of the guide bush abuts the resilient member. The guide bush is configured to be distally advanced by a fluid delivery device, thereby compressing the resilient member into a flow position and fluidly connecting the inner lumen to the delivery lumen via the aperture.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 6 illustrates a cross-sectional view of the housing of the injection port, in accordance with some embodiments disclosed herein.

FIG. 7 illustrates a perspective view of the guide bush of the injection port, in accordance with some embodiments disclosed herein.

FIG. 8 illustrates a perspective view of a resilient member of the injection port, in accordance with some embodiments disclosed herein.

DETAILED DESCRIPTION

In the following detailed description, numerous specific details are set forth to provide a full understanding of the subject technology. The subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

Needle-free connectors are essential devices to deliver fluid to a patient via an intravenous (IV) catheter. Needle-free connectors may be used in general patient populations, including neonatal, pediatric, and adult patients. Integrating needle-free connectors with typical control valves or injection ports has drawbacks. For example, an ordinary injection port would leave the fluid exposed to the environment when the needle-free connector is withdrawn from the injection port. This can result in fluid leaking out of the injection port, which can lead to time spent on otherwise unnecessary cleanup, wasted medication, or premature replacement of an IV cannula. The following devices and methods provide design modifications to overcome the foregoing issues.

Figure 1:
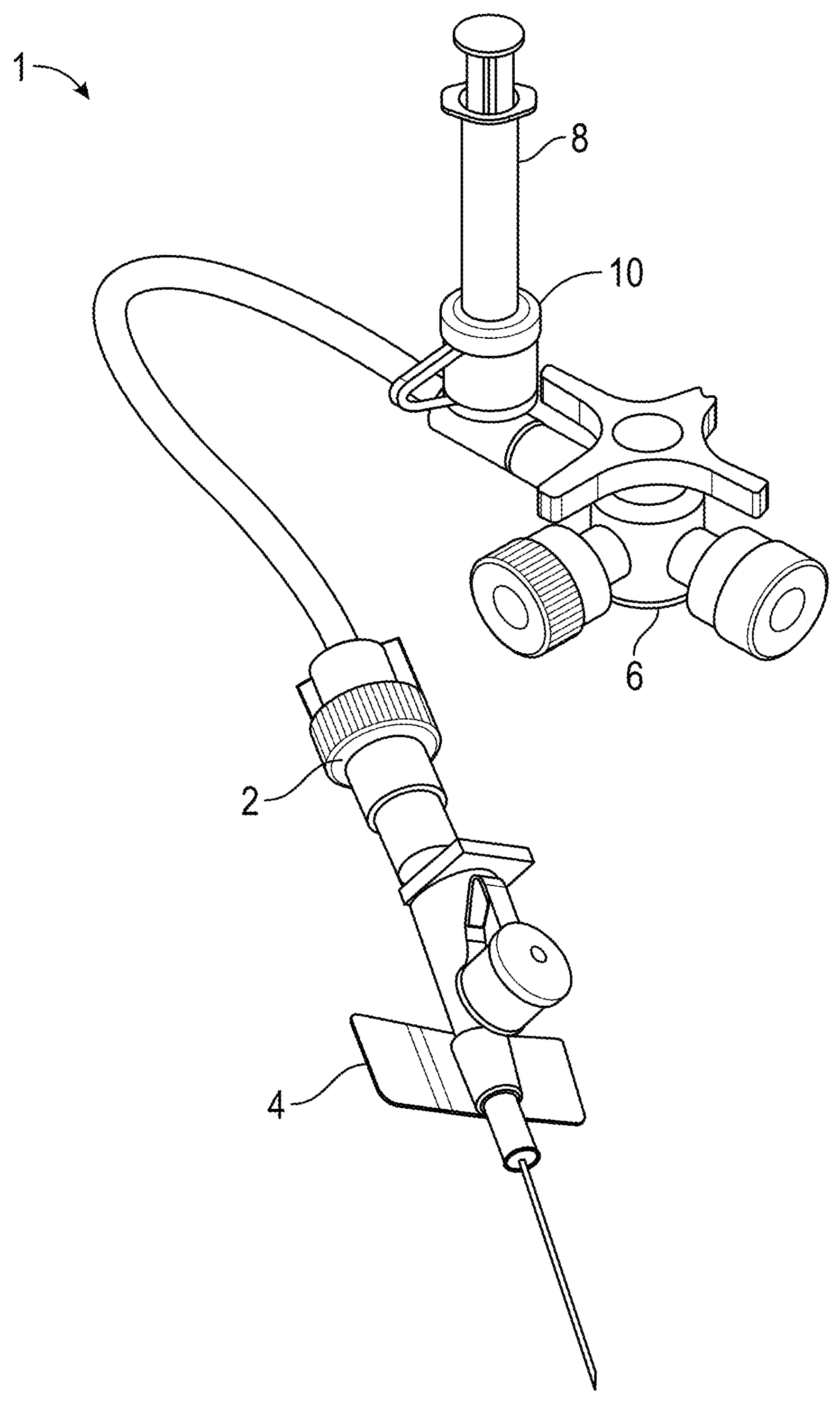
FIG. 1 illustrates a fluid connection device connected to a fluid delivery device and an IV cannula, in accordance with some embodiments disclosed herein.

Referring now to the figures, FIG. 1 illustrates a fluid connection device connected to a fluid delivery device and an IV cannula, in accordance with some embodiments disclosed herein. The fluid connection device 1 includes an IV port 2, a stopcock 6, and an injection port 10. The IV port 2 can be coupled to an IV cannula 4, as shown in FIG. 1, or to an extension tube. The stopcock 6 includes at least one port that can be coupled to a fluid delivery device or needleless fluid connector. Finally, the injection port 10 can be connected to a fluid delivery device or needleless fluid connector such as syringe 8. The injection port 10 is discussed in greater detail below.

Figures 2, 3:
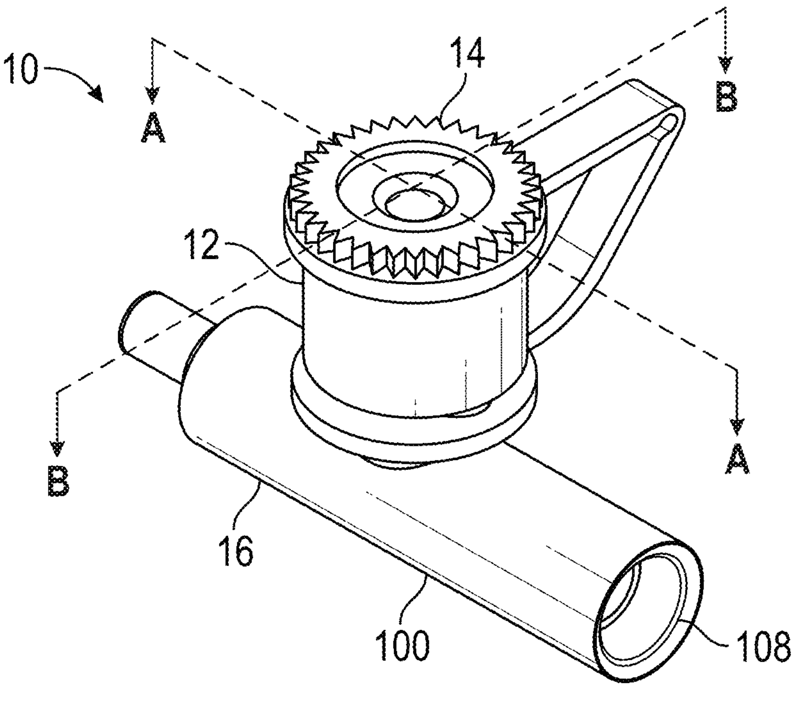
FIG. 2 illustrates an anti-leak injection port for the fluid connection device, in accordance with some embodiments disclosed herein.
FIG. 3 illustrates a cross-sectional view of the injection port for the fluid connection device, in accordance with some embodiments disclosed herein.

FIG. 2 illustrates an anti-leak injection port for the fluid connection device, in accordance with some embodiments disclosed herein. The injection port 10 can be described as having two parts: a reception portion 12 and a delivery portion 16. The reception portion 12 is configured to couple with a fluid delivery device (e.g., syringe 8 shown in FIG. 1), and the delivery portion 16 is configured to couple with tubing that leads to fluid delivery ports (e.g., IV port 2 and/or stopcock 6 shown in FIG. 1). The reception portion 12 has a cap 14, which can be removed to expose a reception lumen (not shown) inside the reception portion 12. The delivery portion 16 has a delivery lumen 108 that can be fluidly connected to the IV port 2 and the stopcock 6 (shown in FIG. 1).

FIG. 3 illustrates a cross-sectional view of the injection port for the fluid connection device, in accordance with some embodiments disclosed herein. The cross-section is taken along the line A-A in FIG. 2. The injection port 10 is made up of a housing 100, a guide bush 200, and a resilient member 300. As shown, the housing 100 includes a reception lumen 102 and a delivery lumen 108. The reception lumen 102 is transverse to the delivery lumen 108. Optionally, the reception lumen 102 is perpendicular to the delivery lumen 108. The reception lumen 102 intersects the delivery lumen 108 at the distalmost end of the reception lumen 102. This intersection is shown in greater detail in FIG. 6, which is discussed below.

Figure 4A:
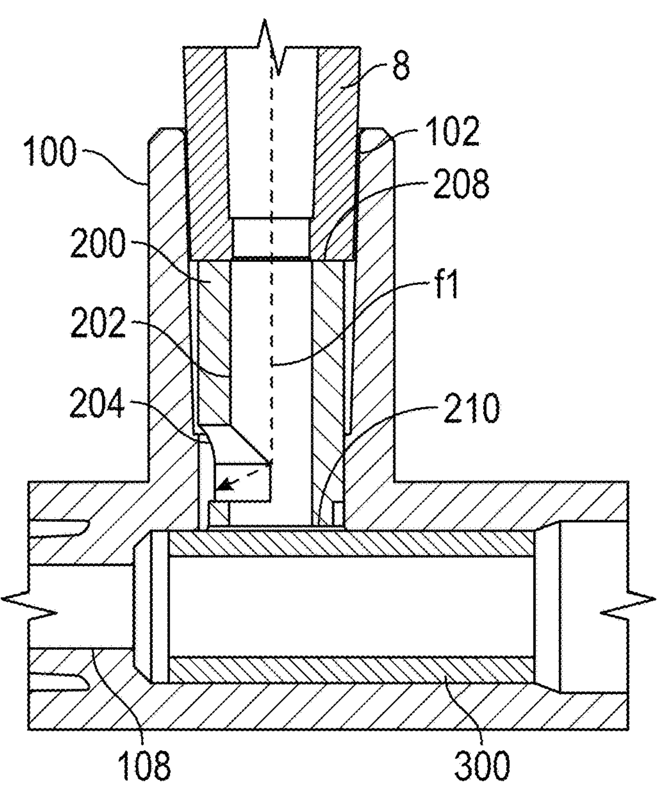
FIG. 4A illustrates a cross-sectional view of the injection port with a fluid delivery device coupled to the guide bush and the resilient member in the default position, in accordance with some embodiments disclosed herein.
Figure 4B:
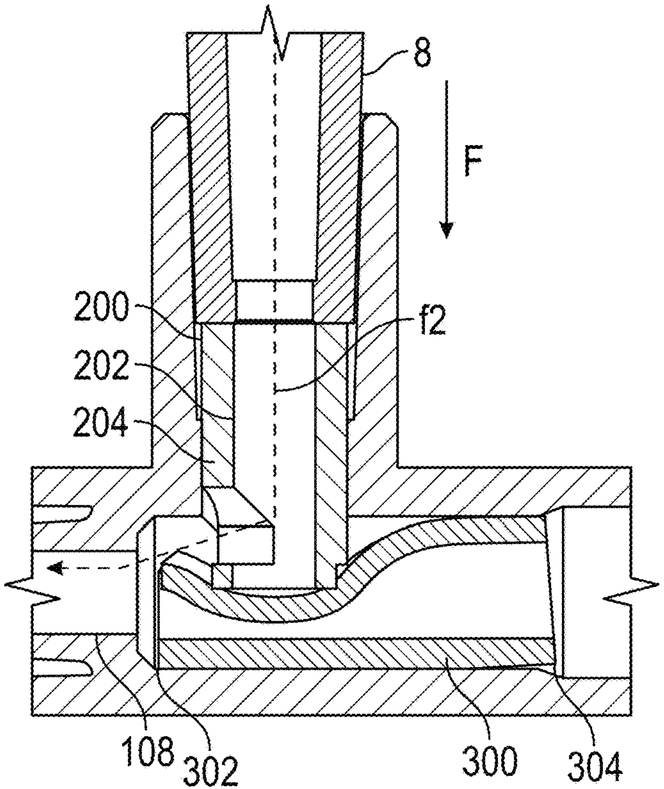
FIG. 4B illustrates a cross-sectional view of the injection port with the fluid delivery device displacing the guide bush such that the guide bush compresses the resilient member into the flow position, in accordance with some embodiments disclosed herein.

As described above with respect to FIG. 1, the injection port 10 is configured to receive a fluid delivery device such as syringe 8. In particular, the fluid delivery device is received within the reception lumen 102 of the housing 100 at the guide bush 200. (This is shown in FIGS. 4A and 4B, which are discussed below.)

The guide bush 200 is positioned within the reception lumen 102 of the housing 100. The guide bush 200 has a generally cylindrical shape, but other shapes are also possible. The shape and height of the guide bush 200 can be adjusted to fit within housings 100 with different shapes and sizes. In some embodiments, the guide bush 200 is shorter than the reception portion 12 of the housing 100 so that a fluid delivery device (e.g., syringe 8 in FIG. 1) can couple with the guide bush 200 inside the reception lumen 102. Optionally, the guide bush 200 couples with the fluid delivery device outside of the housing 100.

The guide bush 200 has an inner lumen 202. The inner lumen 202 can extend along the entire length of the guide bush 200 (as shown in FIG. 3) or only along part of the length of the guide bush 200. In some embodiments, the inner lumen 202 is parallel to the reception lumen 102. The inner lumen 202 is configured to receive fluid from a fluid delivery device (e.g., syringe 8 in FIG. 1) and is fluidly connected to the aperture 204.

The aperture 204 is a hole in the outer surface of the guide bush 200 that extends into the inner lumen 202 of the guide bush 200, such that fluid received from the fluid delivery device at the proximal end of the guide bush 200 is also received at the aperture 204. As shown in FIG. 3, the aperture 204 is positioned at a distal portion of the guide bush 200. In some embodiments, the aperture 204 can be positioned at a distal end of the guide bush 200, such that the aperture 204 is a notch or recess at the distal end of the guide bush 200.

The guide bush 200 abuts the resilient member 300. The distal end of the guide bush 200 contacts an outer surface of the resilient member 300. The resilient member 300 bears radially outwardly against the delivery lumen 108 of the housing 100. In this position (which can be referred to as the default position), the resilient member 300 restricts fluid flow between the reception lumen 102 and the delivery lumen 108. The resilient member 300 can also be displaced into a flow position by the guide bush 200 because the resilient member 300 is made of an elastic material. These two positions are illustrated in FIGS. 4A and 4B and are described in greater detail below.

FIG. 4A illustrates a cross-sectional view of the injection port with a fluid delivery device coupled to the guide bush and the resilient member in the default position, in accordance with some embodiments disclosed herein. As shown, a fluid delivery device 8 is inserted into the reception lumen 102 of the housing 100. The fluid delivery device 8 is coupled to a proximal end 208 of the guide bush 200 and delivers fluid to the inner lumen 202 of the guide bush 200. In FIG. 4A, the distal end 210 of the guide bush 200 rests on the resilient member 300. The resilient member 300 is still pressed radially against the delivery lumen 108 and is still in the default position, which means that the delivery lumen 108 is not fluidly connected to the fluid delivery device 8. This also means that the fluid from the fluid delivery device 8 reaches the aperture 204 of the guide bush 200 and stops there. This is illustrated by the first fluid flow path f1 in FIG. 4A.

FIG. 4B illustrates a cross-sectional view of the injection port with the fluid delivery device displacing the guide bush such that the guide bush compresses the resilient member into the flow position, in accordance with some embodiments disclosed herein. A force F is applied to the fluid delivery device 8, which distally advances the guide bush 200 into the resilient member 300. When the guide bush 200 is distally advanced, the resilient member 300 becomes compressed and transitions into the flow position. In the flow position, the aperture 204 of the guide bush 200 is fluidly connected to the delivery lumen 108. (This is also shown in FIG. 5B, which is discussed below.) As a result, the fluid from the fluid delivery device 8 goes through the inner lumen 202 of the guide bush 200, out the aperture 204, and into the delivery lumen 108. This is illustrated by the second fluid flow path f2.

As shown in FIGS. 3, 4A, and 4B, the guide bush 200 contacts and compresses the resilient member 300 at a position that is closer to the first end 302 than the second end 304. This positioning of the guide bush 200 near the first end 302 of the resilient member 300 facilitates fluid flow forwards (towards the stopcock 6 in FIG. 1) along the second fluid flow path f2 instead of backwards (towards the IV port 2 in FIG. 1) because the second end 304 of the resilient member 300 still bears radially outward against the delivery lumen 108, even when the resilient member 300 is in the flow position. Optionally, the guide bush 200 can contact and compress the resilient member 300 at a position that is closer to the second end 304 than the first end 302, which would facilitate backwards fluid flow.

The resilient member 300 is made of an elastic material (e.g., silicon) that is biased towards the default position. Therefore, as the fluid delivery device 8 is proximally withdrawn, the resilient member 300 immediately begins to expand and return to the default position shown in FIG. 4A. Due to the resilient, elastic nature of the resilient member 300, when the fluid delivery device 8 is withdrawn from the housing 100, the delivery lumen 108 is blocked off from the environment. This means that the fluid, which is now in the delivery lumen 108, will not leak back up the inner lumen 202 of the guide bush 200 and out of the injection port.

FIGS. 3, 4A, and 4B illustrate that the aperture 204 of the guide bush 200 is not aligned with the first end 302 of the resilient member 300. This positioning of the guide bush 200 relative to the resilient member 300 restricts fluid from reentering the inner lumen 202 of the guide bush 200 and leaking out of the injection port when the fluid delivery device 8 is withdrawn from the injection port. Because the aperture 204 is not aligned with the first end 302 of the resilient member 300, the first end 302 returns to bearing radially outward against the delivery lumen 108 (and sealing the delivery lumen 108 off from the aperture 204 and the inner lumen 202) before the fluid delivery device 8 and the guide bush 200 are completely withdrawn.

Figure 5A:
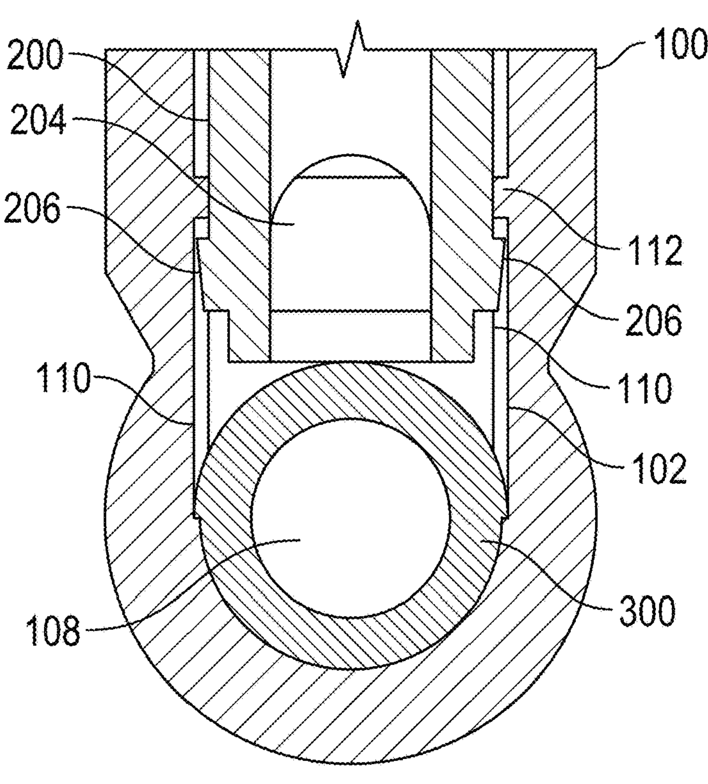
FIG. 5A illustrates a cross-sectional view of the injection port with the resilient member in the default position, in accordance with some embodiments disclosed herein.
Figure 5B:
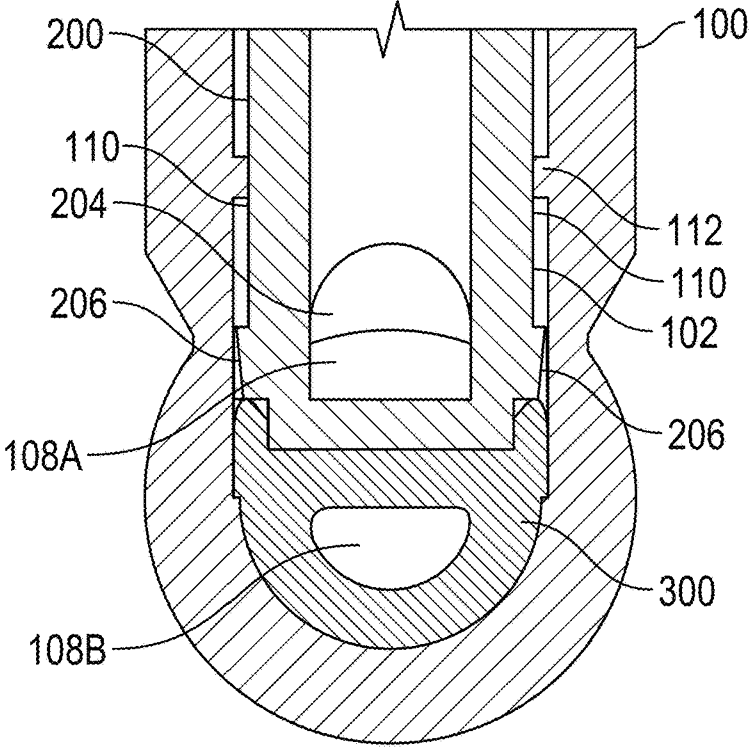
FIG. 5B illustrates a cross-sectional view of the injection port with the resilient member in the flow position, in accordance with some embodiments disclosed herein.

FIG. 5A illustrates a cross-sectional view of the injection port with the resilient member in the default position, in accordance with some embodiments disclosed herein. The cross-section is taken along the line B-B in FIG. 2. As described above with respect to FIG. 4A, the guide bush 200 rests atop the resilient member 300 such that the aperture 204 of the guide bush 200 is not fluidly connected to the delivery lumen 108.

This view of the housing 100 and the guide bush 200 also illustrates the key and slot features that movably couple the guide bush 200 to the housing 100. In particular the guide bush 200 has keys 206 that movably couple to slots 110 in the reception lumen 102 of the housing 100. The keys 206 slide distally along the slots 110 when the guide bush 200 is distally advanced towards the resilient member 300 by the fluid delivery device. The keys 206 also slide proximally along the slots 100 when the guide bush 200 is proximally advanced back up the inner lumen when the resilient member 300 rebounds to the default position. The slot and key configuration can prevent the guide bush 200 from rotating inside the reception lumen 102 of the housing 100, which helps ensure that the aperture 204 remains properly oriented relative to the delivery lumen 108. Optionally, the housing 100 has keys that correspond with slots on the guide bush 200.

In some embodiments, the housing 100 can also have keys 112 at the proximal end of the slots 110 that prevent the guide bush 200 from sliding out of the housing 100. Optionally, the keys 112 can be positioned such that the guide bush 200 maintains constant contact with the resilient member 300.

FIG. 5B illustrates a cross-sectional view of the injection port with the resilient member in the flow position, in accordance with some embodiments disclosed herein. The guide bush 200 is distally advanced by a fluid delivery device (e.g., syringe 8 in FIG. 1) until the guide bush 200 compresses the resilient member 300. As shown, when the resilient member 300 is compressed into the flow position, the aperture 204 of the guide bush 200 is exposed to the delivery lumen 108 of the housing 100—thus fluidly connecting the fluid delivery device, the inner lumen of the guide bush 200, the aperture 204, and the delivery lumen 108. Notably, in FIG. 5B, the aperture 204 is not exposed to the entirety of the delivery lumen 108. As shown, the aperture 204 is only exposed to a first part of the delivery lumen 108A, while the second part of the delivery lumen 108B is still sealed off by the resilient member 300.

As the guide bush 200 is distally advanced by the fluid delivery device, the keys 206 of the guide bush 200 slide distally along the slots 110 that are positioned in the inner lumen 102 of the housing 100. When the fluid delivery device is withdrawn, the keys 206 slide proximally back up the slots 110. In some embodiments, the keys 206 of the guide bush 200 slide proximally up the slots 110 until the keys 206 reach the keys 112 that protrude from the inner lumen 102 of the housing 100. In other embodiments, the keys 206 of the guide bush 200 stop sliding along the slots 110 before reaching the keys 112 of the housing 100.

FIG. 6 illustrates a cross-sectional view of the housing of the injection port, in accordance with some embodiments disclosed herein. This cross-section is taken along the line A-A in FIG. 2. The housing 100 can be made of polycarbonate or other rigid, biocompatible materials.

The housing 100 has a reception lumen 102 that is configured to receive a guide bush (e.g., guide bush 200 shown in FIGS. 3-5B) and a fluid delivery device (e.g., syringe 8 shown in FIG. 1 and fluid delivery device 8 shown in FIGS. 4A and 4B). The housing 100 also has a delivery lumen 108 that is configured to receive a resilient member (e.g., resilient member 300 shown in FIGS. 3-5B). The reception lumen 102 is transverse to the delivery lumen 108. The reception lumen 102 intersects the delivery lumen 108 at a distalmost end 104 of the reception lumen 102.

The housing 100 also includes slots 110, as described above with respect to FIGS. 5A and 5B. The slots 110 shown in FIG. 6 extend from a distal portion of the reception lumen 102, beyond the distalmost end 104 of the reception lumen, and into the delivery lumen 108. In other embodiments, the slots 110 do not extend into the delivery lumen 108. In some embodiments, the housing 100 includes only one slot 110. In other embodiments, the housing 100 includes two slots 110. Optionally, the housing 100 includes three or more slots 110. In some embodiments, the slots 110 are positioned symmetrically around the reception lumen 102. In other embodiments, the slots 110 are positioned asymmetrically around the reception lumen 102.

In FIG. 6, the delivery lumen 108 of the housing 100 has different sections having different diameters. The delivery lumen 108 can be tapered and have a diameter that continuously changes. The delivery lumen 108 can also have multiple sections each with its own diameter that is different from the other sections but consistent within any given section. In the embodiment shown, the section of the delivery lumen 108 that intersects the reception lumen 102 has a diameter that is specially fitted to the resilient member (i.e., resilient member 300 shown in FIGS. 3-5B and 8). This ensures that the resilient member does not slide along the delivery lumen 108.

FIG. 7 illustrates a perspective view of the guide bush of the injection port, in accordance with some embodiments disclosed herein. The guide bush 200 can be made of polypropylene, an acrylic-based copolymer, or any other rigid material. The guide bush 200 has an inner lumen 202, an aperture 204 positioned at or near the distal end of the guide bush 200, and keys 206 protruding from the outer surface of the guide bush 200 at or near the distal end of the guide bush 200.

In the embodiment shown in FIGS. 3-5B and 7, the inner lumen 202 extends through the entire length of the guide bush 200 and is fluidly connected to the aperture 204. That is, the entirety of the guide bush 200, from the proximal end to the distal end, is hollow, which can reduce the amount of material required to manufacture the guide bush 200 and can make the injection port lighter. In other embodiments, the inner lumen 202 only extends along part of the length of the guide bush 200. For example, the inner lumen 202 can extend from the proximal end of the guide bush 200 and only reach the aperture 204, such that the inner lumen 202 and the aperture 204 are still fluidly connected. In this embodiment, the distal end of the guide bush 200 would be closed, which can help control the flow path of fluid delivered by the fluid delivery device.

In the embodiment shown in FIGS. 3-5B and 7, the aperture 204 is positioned near the distal end of the guide bush 200 and has a generally semi-circular shape. Other positions and shapes are also possible. For example, the aperture 204 can be positioned adjacent to the distal end of the guide bush 200, such that the aperture 204 is cut out of the base of the guide bush 200 and is immediately adjacent to the resilient member when the injection port is assembled (as shown in FIGS. 3-5B). The aperture 204 can also be fully circular, square, rectangular, etc.

The aperture 204 can also have different sizes. As shown in FIG. 7, the guide bush 200 has a height $H_1$ and the aperture 204 has a height $H_2$. In the embodiment shown in FIGS. 3-5B and 7, $H_2$ is about one-third the height of $H_1$. In some embodiments, $H_2$ is approximately one-fourth to one-half the height of $H_1$. Other size ratios are also possible.

The guide bush also includes keys 206. The size and number of keys 206 on the guide bush 200 can correspond to the size and number of slots in the housing (i.e., the slots 110 in the reception lumen 102 of housing 100, as shown in FIG. 6). The keys 206 can fit inside and slide along a slot inside the reception lumen of the housing. The keys 206 are configured to prevent the guide bush 200 from rotating within the housing of the injection port, which helps ensure that the aperture 204 is properly oriented relative to the delivery lumen (i.e., the delivery lumen 108 of the housing 100, as shown in FIG. 6).

The keys 206 protrude from an outer surface of the guide bush 200 at different positions. In some embodiments, the keys 206 can extend proximally from the distal end of the guide bush 200. In the embodiment shown in FIG. 7, the keys are positioned at a distal portion of the guide bush 200, not reaching the distal end of the guide bush 200. In addition to having different positions, the keys 206 can also have different sizes. In FIG. 7, the keys 206 are shorter than the aperture 204. In other embodiments, the keys 206 can be taller than the aperture 204. The keys 206 can also have different widths and depths, which can correspond to the slots in the reception lumen of the housing.

The guide bush 200 has a proximal diameter $D_p$ and a distal diameter $D_d$. As shown in FIG. 7, $D_d$ is smaller than $D_p$ because the distal portion of the guide bush 200 is a step in relative to the remainder of the guide bush 200. This reduces friction between the outer surface of the guide bush 200 and the reception lumen of the housing as the guide bush 200 slides within the reception lumen of the housing. The smaller distal diameter $D_d$ also improves fluid flow between the inner lumen 202 of the guide bush 200 and the delivery lumen of the housing when the resilient member is in the flow position by reducing the amount of guide bush material in the clearance formed in the delivery lumen when the resilient member is compressed into the flow position.

FIG. 8 illustrates a perspective view of a resilient member of the injection port, in accordance with some embodiments disclosed herein. The resilient member 300 is made of an elastic material such as silicon. The resilient member 300 has a generally cylindrical shape and a hollow interior (i.e., the resilient member 300 can be tube-shaped). The resilient member 300 has an outer diameter $D_o$ and an inner diameter $D_i$. The ratio of $D_o$ to $D_i$ is approximately 1.5. In some embodiments, the ratio of $D_o$ to $D_i$ is approximately 1.0 to 2.0. In other embodiments, the ratio of $D_o$ to $D_i$ is greater than 2.0.

The thickness of the hollow tube that makes up the resilient member 300 changes as the ratio of $D_o$ to $D_i$ changes. The thickness of the hollow tube is directly related to the resiliency of the resilient member 300. That is, a thicker hollow tube means that the resilient member 300 is more resilient and more biased towards the default position than a resilient member 300 with a thinner hollow tube.

The present disclosure also includes a method of using the injection port. Before a fluid delivery device is coupled with the injection port, the guide bush rests atop the resilient member, and the resilient member is in a default position, wherein the inner lumen and the aperture of the guide bush are sealed off, by the resilient member, from the delivery lumen of the housing. With reference to FIGS. 4A, a fluid delivery device 8 is inserted into the injection port. In particular, the fluid delivery device 8 is inserted into the reception lumen 102 of the housing 100 via an opening at the proximal end of the housing 100. The fluid delivery device 8 engages with the proximal end 208 of the guide bush 200.

In FIG. 4B, a force F is applied to the fluid delivery device 8, which distally advances the guide bush 200. The keys 206 in the guide bush 200 (shown in FIGS. 5A-5B) slide along the slots 110 of the housing 100 (shown in FIGS. 5A-5B) as the guide bush 200 moves within the reception lumen 102 of the housing 100. Additionally, when the guide bush 200 is distally advanced, the guide bush 200, which is rigid, applies the force F to the outer surface of the resilient member 300, which is elastic. As a result, the resilient member 300 transitions from the default position (shown in FIG. 4A) to a flow position (shown in FIG. 4B). In the flow position, the fluid delivery device 8, the inner lumen 202 of the guide bush 200, the aperture 204 of the guide bush 200, and the delivery lumen 108 of the housing 100 are in fluid communication with each other. This means that in the flow position, fluid will travel from the fluid delivery device 8 to the delivery lumen 108 (along the second flow path f2).

When the fluid delivery is complete, the fluid delivery device 8 is withdrawn from the reception lumen 102 of the housing 100. As a result, the force F is removed from the guide bush 200 and the resilient member 300. The resilient member 300 exerts a resilient or rebound force on the guide bush 200 as the resilient member 300 returns to the default position. The elasticity of the resilient member 300 ensures that the second flow path f2 is quickly closed off, which restricts fluid from returning up the inner lumen 202 of the guide bush 200 and leaking out of the injection port.

The present disclosure also provides a method of manufacturing the anti-leak injection port. The method begins by providing a housing (which can include molding the housing), such as the housing 100 shown in FIG. 6. The housing 100 has at least two lumens: a reception lumen 102 and a delivery lumen 108.

The reception lumen 102 can have a consistent diameter or a tapered diameter. Optionally, the reception lumen 102 can have multiple sections, each with a consistent diameter that is different from at least one other section. The reception lumen 102 is transverse relative to the delivery lumen 108 and is fluidly connected to the delivery lumen 108.

The delivery lumen 108 can have multiple sections, each with a diameter that is different from at least one other section. Any given section can have a tapered diameter or a consistent/uniform diameter. Optionally, the delivery lumen 108 is not broken up into multiple sections and has a tapered diameter. In embodiments where the delivery lumen 108 is made up of one section with a tapered diameter, the resilient member (the manufacture of with is described in greater detail below) has a corresponding tapered diameter so that the resilient member can fit snugly inside the delivery lumen 108.

Providing the housing 100 also includes inserting one or more slots 110 into the reception lumen 102 of the housing 100. The slots 110 can be cut into the surface of the reception lumen 102 or molded into the housing 100 when the housing 100 is molded. The slots 110 start at a distal portion of the reception lumen 102, near the delivery lumen 108, and extend distally towards the delivery lumen 108. In some embodiments, the slots 110 extend into the delivery lumen 108.

Next, a resilient member is provided, such as the resilient member 300 shown in FIG. 8. The resilient member 300 is generally cylindrical, hollow, and made up of an elastic material such as silicon. The resilient member 300 is positioned inside the delivery lumen 108 of the housing 100. The resilient member 300 is sized to fit snugly within the delivery lumen 108 and, in a default position, bears radially outward against the delivery lumen 108.

After the resilient member 300 is placed inside the delivery lumen 108, a guide bush, such as guide bush 200 shown in FIG. 7, is provided. The guide bush 200 includes an inner lumen 202, an aperture 204 in fluid communication with the inner lumen 202, and one or more keys 206 protruding from an outer surface of the guide bush 200. The guide bush 200 is made of a rigid material and can be molded to include the inner lumen 202, the aperture 204, and the keys 206. Optionally, the guide bush 200 begins as a hollow cylinder and is manufactured by cutting the aperture 204 out of the outer surface of the hollow cylinder and applying keys 206 to the outer surface of the hollow cylinder. Optionally, the guide bush 200 begins as a solid cylinder, the inner lumen 202 and the aperture 204 are cut out of the solid cylinder, and the keys 206 are applied to the outer surface of the solid cylinder.

Finally, the guide bush 200 is positioned within the reception lumen 102 of the housing 100. This includes coupling the keys 206 of the guide bush 200 to the slots 110 of the housing 100. The guide bush 200 rests on top of the resilient member 300 while the resilient member 300 is in the default position.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 9, or clause 16. The other clauses can be presented in a similar manner.

Clause 1. An anti-leak injection port for a fluid connection device, the injection port comprising: a housing comprising a reception lumen and a delivery lumen, wherein the delivery lumen is transverse to the reception lumen and intersects a distalmost end of the reception lumen; a guide bush disposed within the reception lumen and configured to receive a fluid delivery device, wherein the guide bush comprises an inner lumen and an aperture fluidly connected to the inner lumen; and a resilient member disposed within the delivery lumen and configured to restrict fluid flow through the delivery lumen in a default position and to fluidly connect the fluid delivery device and the delivery lumen in a flow position, wherein the resilient member is configured to be compressed into the flow position when the guide bush receives the fluid delivery device.

Clause 2. The injection port of Clause 1, wherein the injection port is configured to fluidly connect the fluid delivery device to one or more of an extension tube, an IV cannula, or a stopcock.

Clause 3. The injection port of Clause 1, wherein the housing comprises slots, and the guide bush comprises keys that are movably coupled to the slots.

Clause 4. The injection port of Clause 3, wherein the slots are positioned at a distal portion of the reception lumen and adjacent to the delivery lumen.

Clause 5. The injection port of Clause 3, wherein the slots and the keys are configured to facilitate continuous contact between the guide bush and the resilient member.

Clause 6. The injection port of Clause 3, wherein the keys are configured to advance distally along the slots when the guide bush receives the fluid delivery device and are configured to slide proximally along the slots when the fluid delivery device is withdrawn from the guide bush.

Clause 7. The injection port of Clause 1, wherein the guide bush comprises a material that is more rigid than the resilient member.

Clause 8. The injection port of Clause 1, wherein the guide bush receives the fluid delivery device at a proximal end of the guide bush and contacts the resilient member at a distal end of the guide bush.

Clause 9. The injection port of Clause 1, wherein the guide bush is configured to be advanced distally by the fluid delivery device to compress the resilient member from the default position into the flow position.

Clause 10. The injection port of Clause 1, wherein the guide bush has a first height, the aperture has a second height, and the ratio of the first height to the second height is about 3.

Clause 11. The injection port of Clause 1, wherein the aperture is positioned at a distal portion of the guide bush.

Clause 12. The injection port of Clause 1, wherein the aperture is configured to fluidly connect the inner lumen and the delivery lumen when the guide bush receives the fluid delivery device and compresses the resilient member into the flow position.

Clause 13. The injection port of Clause 1, wherein the resilient member comprises a hollow cylinder.

Clause 14. The injection port of Clause 1, wherein the hollow cylinder comprises an inner diameter and an outer diameter, and the ratio of the outer diameter to the inner diameter is about 1.5.

Clause 15. The injection port of Clause 1, wherein the resilient member is configured to bear radially outward against the delivery lumen.

Clause 16. The injection port of Clause 1, wherein the resilient member comprises an elastic material and is configured to resiliently transition from the flow position to the default position when the fluid delivery device is withdrawn from the guide bush.

Clause 17. A guide bush for an anti-leak injection port, the guide bush configured to be movably coupled to a housing and comprising an inner lumen, an aperture that is fluidly connected to the inner lumen, and keys protruding from an outer surface of the guide bush, wherein the guide bush is configured to receive a fluid delivery device be distally advanced to displace a resilient member coupled to the housing and facilitate fluid flow through the housing.

Clause 18. The guide bush of Clause 17, wherein the keys are configured to movably couple with slots in the housing of the anti-leak injection port.

Clause 19. The guide bush of Clause 17, wherein the aperture is positioned on a distal portion of the guide bush.

Clause 20. A method for manufacturing an anti-leak injection port, the method comprising: providing a housing comprising a reception lumen, slots on a surface of a distal portion of the reception lumen, and a delivery lumen that is transverse to the reception lumen and intersects a distalmost end of the reception lumen; providing a resilient member, wherein the resilient member is hollow and cylindrical; positioning the resilient member within the delivery lumen, wherein the resilient member bears outwardly against the delivery lumen in a default position; providing a guide bush comprising an inner lumen, an aperture fluidly connected to the inner lumen, and keys protruding from an outer surface of a distal portion of the guide bush; and positioning a guide bush within the reception lumen such that the keys are movably coupled to the slots and a distal end of the guide bush abuts the resilient member, wherein the guide bush is configured to be distally advanced by a fluid delivery device, thereby compressing the resilient member into a flow position and fluidly connecting the inner lumen to the delivery lumen via the aperture.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear," and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An anti-leak injection port for a fluid connection device, the injection port comprising: a housing comprising a reception lumen and a delivery lumen, wherein the delivery lumen is transverse to the reception lumen and intersects a distalmost end of the reception lumen; a guide bush disposed within the reception lumen and configured to receive a fluid delivery device, wherein the guide bush comprises an inner lumen and an aperture fluidly connected to the inner lumen; and a resilient member disposed within the delivery lumen and configured to restrict fluid flow through the delivery lumen in a default position and to fluidly connect the fluid delivery device and the delivery lumen in a flow position, wherein the resilient member is configured to be compressed into the flow position when the guide bush receives the fluid delivery device; wherein the housing comprises slots, and the guide bush comprises keys that are movably coupled to the slots.

2. The injection port of claim 1, wherein the injection port is configured to fluidly connect the fluid delivery device to one or more of an extension tube, an IV cannula, or a stopcock.

3. The injection port of claim 1, wherein the slots are positioned at a distal portion of the reception lumen and adjacent to the delivery lumen.

4. The injection port of claim 1, wherein the slots and the keys are configured to facilitate continuous contact between the guide bush and the resilient member.

5. The injection port of claim 1, wherein the keys are configured to advance distally along the slots when the guide bush receives the fluid delivery device and are configured to slide proximally along the slots when the fluid delivery device is withdrawn from the guide bush.

6. The injection port of claim 1, wherein the guide bush comprises a material that is more rigid than the resilient member.

7. The injection port of claim 1, wherein the guide bush receives the fluid delivery device at a proximal end of the guide bush and contacts the resilient member at a distal end of the guide bush.

8. The injection port of claim 1, wherein the guide bush is configured to be advanced distally by the fluid delivery device to compress the resilient member from the default position into the flow position.

9. The injection port of claim 1, wherein the guide bush has a first height, the aperture has a second height, and the ratio of the first height to the second height is about 3.

10. The injection port of claim 1, wherein the aperture is positioned at a distal portion of the guide bush.

11. The injection port of claim 1, wherein the aperture is configured to fluidly connect the inner lumen and the delivery lumen when the guide bush receives the fluid delivery device and compresses the resilient member into the flow position.

12. The injection port of claim 1, wherein the resilient member comprises a hollow cylinder.

13. The injection port of claim 1, wherein the hollow cylinder comprises an inner diameter and an outer diameter, and the ratio of the outer diameter to the inner diameter is about 1.5.

14. The injection port of claim 1, wherein the resilient member is configured to bear radially outward against the delivery lumen.

15. The injection port of claim 1, wherein the resilient member comprises an elastic material and is configured to resiliently transition from the flow position to the default position when the fluid delivery device is withdrawn from the guide bush.

* * * * *